United States Patent
Cecchi et al.

(10) Patent No.: US 11,631,488 B2
(45) Date of Patent: Apr. 18, 2023

(54) DIALOGUE GENERATION VIA HASHING FUNCTIONS

(71) Applicant: INTERNATIONAL BUSINESS MACHINES CORPORATION, Armonk, NY (US)

(72) Inventors: Guillermo Cecchi, New York, NY (US); Irina Rish, Rye Brook, NY (US); Sahil Garg, Los Angeles, CA (US)

(73) Assignee: International Business Machines Corporation, Armonk, NY (US)

( * ) Notice: Subject to any disclaimer, the term of this patent is extended or adjusted under 35 U.S.C. 154(b) by 651 days.

(21) Appl. No.: 16/571,235

(22) Filed: Sep. 16, 2019

(65) Prior Publication Data

US 2021/0081813 A1    Mar. 18, 2021

(51) Int. Cl.
  G10L 15/22    (2006.01)
  G10L 15/18    (2013.01)
  G16H 20/70    (2018.01)
  G10L 25/78    (2013.01)

(52) U.S. Cl.
  CPC ......... *G16H 20/70* (2018.01); *G10L 15/1815* (2013.01); *G10L 15/22* (2013.01); *G10L 25/78* (2013.01)

(58) Field of Classification Search
  CPC ......... G10L 15/22; G16H 10/60; G16H 50/30
  See application file for complete search history.

(56) References Cited

U.S. PATENT DOCUMENTS

| | | | | |
|---|---|---|---|---|
| 7,801,885 B1* | 9/2010 | Verma | ................. | G06F 16/9535 707/758 |
| 7,835,997 B2 | 11/2010 | Rajkhowa | | |
| 8,423,541 B1* | 4/2013 | Baluja | ................. | G06F 16/9535 707/732 |
| 2014/0337048 A1 | 11/2014 | Brown | | |
| 2018/0211509 A1* | 7/2018 | Ramaci | ................. | G08B 5/36 |
| 2018/0308574 A1 | 10/2018 | Proctor Beauchamp | | |
| 2019/0259500 A1* | 8/2019 | Abou | ................. | H04L 67/22 |
| 2019/0311814 A1* | 10/2019 | Kannan | ................. | G16H 70/20 |

FOREIGN PATENT DOCUMENTS

CN    103400054 A    11/2013

OTHER PUBLICATIONS

Garg, Sahil, et al. "Dialogue Modeling Via Hash Functions: Applications to Psychotherapy." arXiv preprintarXiv:1804.10188 (Apr. 2018). (Year: 2018).*

Garg et al., "Kernelized Hashcode Representations for Relation Extraction", 2019, Association for the Advancement of Artificial Intelligence, (www.aaai.org), pp. 1-13.

Mell et al., "The NIST Definition of Cloud Computing", National Institute of Standards and Technology, Special Publication 800-145, Sep. 2011, pp. 1-7.

* cited by examiner

*Primary Examiner* — Jialong He
(74) *Attorney, Agent, or Firm* — Brandon L. Stephens; Kristofer Leon Haggerty

(57) ABSTRACT

Exemplary embodiments disclose a method, a computer program product, and a computer system for generating dialogue via hashing functions. Exemplary embodiments may include detecting dialogue between one or more participants, converting the dialogue to a hashcode, and determining one or more responses to the dialogue by applying one or more models to the hashcode, wherein the one or more models correlates one or more hashcodes with the one or more responses.

17 Claims, 6 Drawing Sheets

DIALOGUE GENERATION VIA HASHING FUNCTIONS

BACKGROUND

The present invention relates generally to dialogue generation, and more particularly to generating dialogue via hashing functions.

Despite an enormous cost to society, the treatment of mental health conditions relies heavily on non-standardized practices. Such practices rely heavily on therapy sessions with clinicians having a diverse degree of training, the results of which vary in success. In practice, the knowledge that therapists acquire through years of schooling and practice has not been standardized in any way that can be made readily available to both the trained and the novice therapist. Best practices from successful therapists can be transmitted to the mental health community only through a dedicated effort that may interfere with the task of seeing patients, and may not be successful due to the difficulties involved in formalizing intuitive and automated mechanisms.

SUMMARY

Exemplary embodiments disclose a method, a computer program product, and a computer system for generating dialogue via hashing functions. Exemplary embodiments may include detecting dialogue between one or more participants, converting the dialogue to a hashcode, and determining one or more responses to the dialogue by applying one or more models to the hashcode, wherein the one or more models correlates one or more hashcodes with the one or more responses.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION OF THE SEVERAL VIEWS OF THE DRAWINGS

Figure 1:
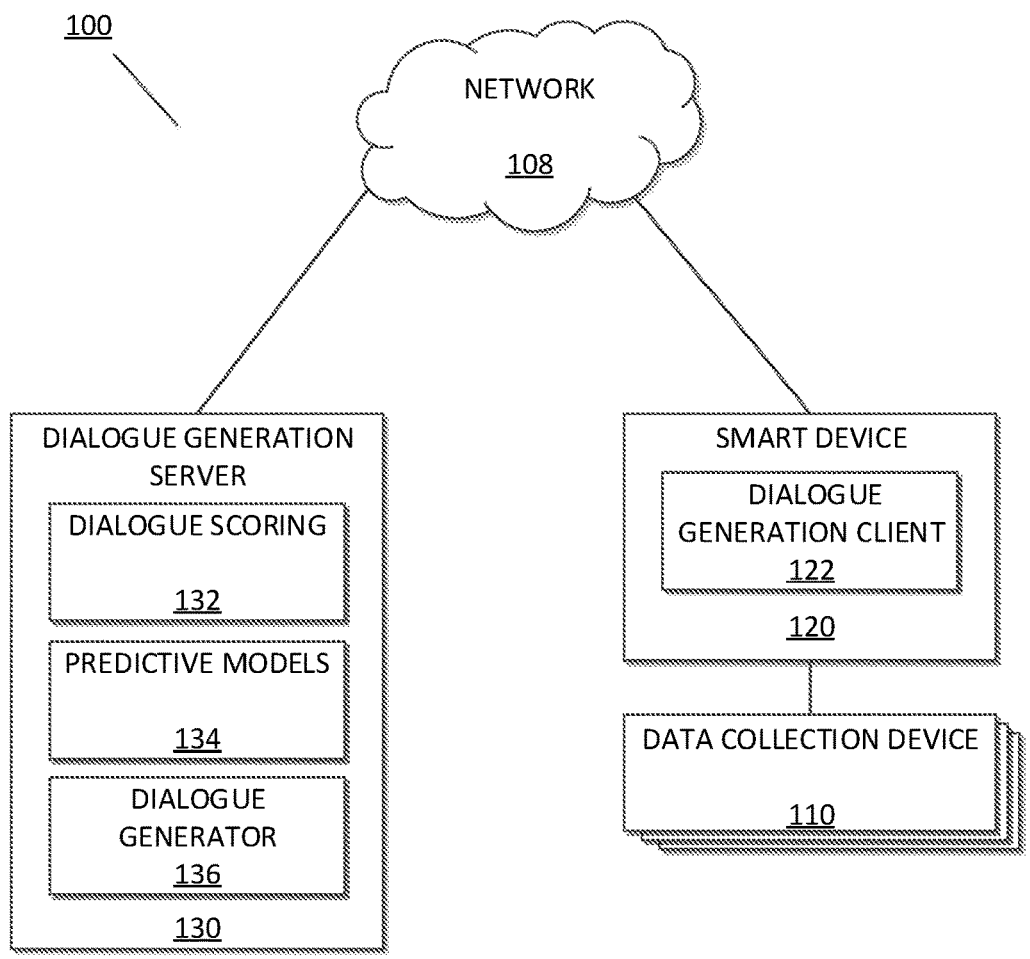
FIG. 1 depicts a schematic diagram of a dialogue generation system 100, in accordance with exemplary embodiments.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete, and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements of various embodiments of the present invention.

Despite an enormous cost to society, the treatment of mental health conditions relies heavily on non-standardized practices. Such practices rely heavily on therapy sessions with clinicians having a diverse degree of training, the results of which vary in success. In practice, the knowledge that therapists acquire through years of schooling and practice has not been standardized in any way that can be made readily available to both the trained and the novice therapist. Best practices from successful therapists can be transmitted to the mental health community only through a dedicated effort that may interfere with the task of seeing patients, and may not be successful due to the difficulties involved in formalizing intuitive and automated mechanisms.

Currently, a recommendation system for the practicing therapist does not exist. There are currently a plethora of chatbots available, but these chatbots lack clinical rigor and fail at effectively engaging patients as they rely mostly on having a full conversational system, which is a computational problem of high complexity that has not yet been solved.

According to exemplary embodiments, a method, computer program product, and system for a dialogue generation system 100 is disclosed. The dialogue generation system 100 presented herein learns best practices in dialogue, for example therapy sessions, and recommends to a topic/answer in real time during a session while also estimating an overall rate of success during the progression of the session.

The dialogue generation system 100 achieves this by utilizing a reduced hashcode representation of an unconstrained, textual dialogue.

As will be described in greater detail forthcoming, the dialogue generation system 100 is utilized in an environment where one or more participants, such as a patient and a therapist, interact with each other using unconstrained textual responses. The dialogue generation system 100 is configured to appreciate the challenges in providing suggested responses, including the fact that responses from a participant can be long and difficult to interpret and that dialogue context must be considered. Moreover, the system is configured to evaluate an inferred response among many other good choices of responses besides the one present in a dataset of recorded therapy sessions.

The dialogue generation system 100 described herein introduces a novel dialogue modelling framework that represents textual responses in a dialogue as binary hashcodes computable using kernel similarity functions as well as neural networks. The motivation behind the idea of using hashcodes as representations of the textual responses in a dialog is as following: while inferring an exact response in the form of text is a hard problem as per the aforementioned reasons, however inferring a generalized representation for a response is relatively easier, as the target to predict becomes lower dimensional. The generalized representation is such that it is interpretable as well as useful for efficient search of text sentences corresponding to the representation. Binary hashcodes have these traits, which is why they are implemented in the dialogue generation system 100 described herein.

Key benefits of the dialogue generation system 100 include improving a quality and effectiveness of dialogue and dialogue generation interactions, increasing an efficiency and effectiveness of computing devices implementing dialogue generation systems, introducing standardized dialogue generation practices, increased availability of standardized dialogue generation practices, increased access to best practices, and automated response generation and suggestion using said best practices. Detailed implementation of the dialogue generation system 100 follows.

FIG. 1 depicts a dialogue generation system 100, in accordance with embodiments of the present invention. In the example embodiment, the dialogue generation system 100 may include one or more data collection devices 110, a smart device 120, and a dialogue generation server 130, all interconnected via a network 108. While, in the example embodiment, programming and data of the present invention are stored and accessed remotely across several servers via the network 108, in other embodiments, programming and data of the present invention may be stored locally on as few as one physical computing device or amongst other computing devices than those depicted.

In the example embodiment, the network 108 may be a communication channel capable of transferring data between connected devices. In the example embodiment, the network 108 is the Internet, representing a worldwide collection of networks and gateways to support communications between devices connected to the Internet. Moreover, the network 108 may include, for example, wired, wireless, and/or fiber optic connections which may be implemented as an intranet network, a local area network (LAN), a wide area network (WAN), or a combination thereof. In further embodiments, the network 108 may be a Bluetooth network, a WiFi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 can be any combination of connections and protocols that will support communications between connected devices.

In the example embodiment, the data collection device 110 may be any device capable of collecting, storing, processing, transmitting, and/or receiving data. In embodiments, for example, the data collection device 110 may be a device within an environment, such as a smart device/wearable (phone, tablet, personal computer, smart watch, smart glasses, etc.), appliance, sensor, camera, microphone, implantable, etc. Moreover, in embodiments, the data collection device 110 may include computing components used for collecting, processing, aggregating, and transmitting data, for example those depicted by FIG. 4. While the one or more data collection devices 110 are shown as a single device, in other embodiments, the data collection devices 110 may be comprised of a cluster or plurality of computing devices, working together or working separately. The data collection devices 110 are described in greater detail as a hardware implementation with reference to FIG. 4, as part of a cloud implementation with reference to FIG. 5, and/or as utilizing functional abstraction layers for processing with reference to FIG. 6.

In the example embodiment, the smart device 120 may include dialogue generation client 122 and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While the smart device 120 is shown as a single device, in other embodiments, the smart device 120 may be comprised of a cluster or plurality of computing devices, working together or working separately. The smart device 120 is described in greater detail as a hardware implementation with reference to FIG. 4, as part of a cloud implementation with reference to FIG. 5, and/or as utilizing functional abstraction layers for processing with reference to FIG. 6.

In the example embodiment, the dialogue generation client 122 may act as a client in a client-server relationship and may be a software and/or hardware application capable of communicating with and providing a user interface to interact with a server via the network 108. Moreover, in the example embodiment, the dialogue generation client 122 is capable of transferring data between the smart device 120, the data collection device 110, the dialogue generation server 130, and other devices via the network 108. In embodiments, the dialogue generation client 122 utilizes various wired and wireless connection protocols for data transmission and exchange, including Bluetooth, 2.4 gHz and 5 gHz internet, near-field communication, Z-Wave, Zigbee, etc.

In the example embodiment, the dialogue generation server 130 may include dialogue scoring 132, predictive models 134, and a dialogue generator 136, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While the dialogue generation server 130 is shown as a single device, in other embodiments, the dialogue generation server 130 may be comprised of a cluster or plurality of computing devices, working together or working separately. The dialogue generation server 130 is described in greater detail as a hardware implementation with reference to FIG. 4, as part of a cloud implementation with reference to FIG. 5, and/or as utilizing functional abstraction layers for processing with reference to FIG. 6.

In the example embodiment, the dialogue scoring 132 may be metrics that rank the effectiveness of dialogue between one or more users. The scoring 132 may relate to qualitative dialogue metrics (i.e. quality, effectiveness, efficiency, turn taking, verbosity, working alliance, etc.), quantitative metrics (i.e. duration, speaking time of respective users, etc.), psychological metrics (i.e. personality types, happiness, sadness, anger, etc.), physiological metrics (i.e. stress, anxiety, hormones, etc.), and other metrics utilized in assessing an effectiveness of a given dialogue. The scoring 132 is described in greater detail with respect to FIG. 2-3.

In the example embodiment, the predictive models 134 may be one or more algorithms capable of transforming an input into an output. In particular, the predictive models 134 may be applied to dialogue input received in the form of unconstrained text and output a suggested response/topic based on the dialogue input. The predictive models 134 may include different models for various topics and subtopics of dialogue, for example therapy, casual conversation, sports conversation, etc., and the predictive models 134 may be configured to maximize an efficiency, effectiveness, or other intended result of the predictive models 134. Moreover, the predictive models 134 may be evaluated and modified/tuned based on the dialogue scoring 132, as well as other feedback loops. The predictive models 134 are described in greater detail with respect to FIG. 2-3.

In the example embodiment, the dialogue generator 136 may be a software and/or hardware application configured to generate dialogue via hashing functions. In particular, the dialogue generator 136 may be configured to initialize a dialogue session and receive pre-dialogue scoring. Moreover, the dialogue generator 136 may be further configured to convert session dialogue into hashcode and apply predictive models to the hashcode. The dialogue generator 136 may be further configured to generate and provide in-dialogue responses based on the applied predictive models before determining whether the session has concluded. Based on determining that the session has concluded, the dialogue generator 136 may be further configured to receive post-dialogue scoring and determine a generated dialogue efficiency based thereon. Lastly, the dialogue generator 136 may be configured to adjust the predictive models based on the determined generated dialogue efficiency.

It will be appreciated that although the scoring 132, the predictive models 134, and the dialogue generator 136 are stored and operated remotely on the dialogue generation server 130 via the network 108, in other embodiments, the aforementioned components may be stored and operated locally, such as on the smart device 120.

Figure 2:
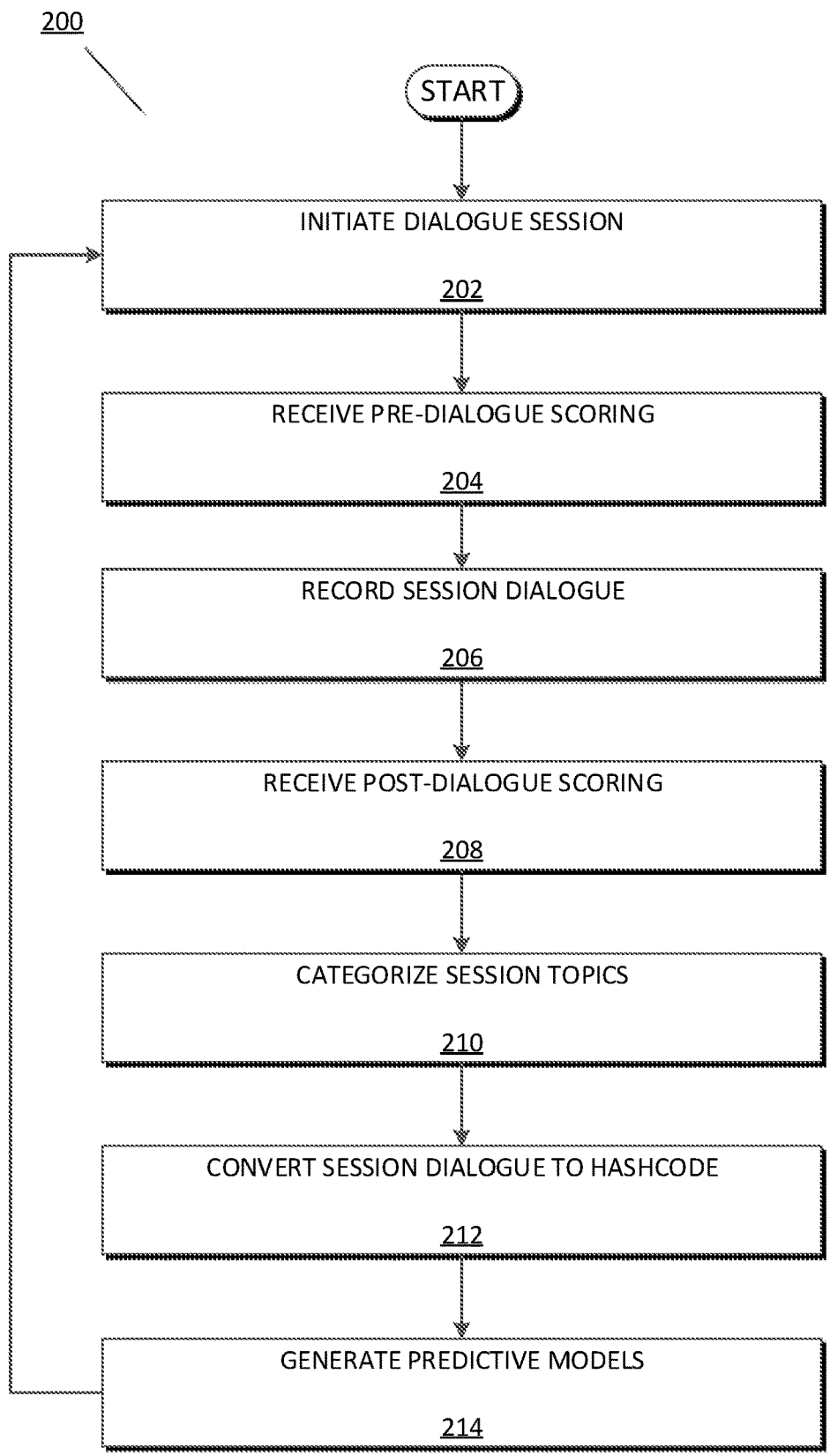
FIG. 2 depicts a flowchart 200 illustrating the training of a dialogue generator 126 of the dialogue generation system 100 in generating dialogue via hashing functions, in accordance with exemplary embodiments.

FIG. 2 depicts a flowchart 200 illustrating the training of a dialogue generator 126 of the dialogue generation system 100 in generating dialogue via hashing functions, in accordance with exemplary embodiments.

The dialogue generator 136 may initiate a dialogue session (step 202). In the example embodiment, initiating the dialogue session may involve the dialogue generator 136 receiving one or more participant registrations and/or a configuration of the dialogue generation system 100, both via the dialogue generation client 122 and the network 108. In particular, the participant registrations may include demographic information of dialogue participants, such as participant name, gender, date of birth, location, etc., as well as other information such as health and diagnosis information, previous interactions with participants and/or the dialogue generation system 100, reasons for utilizing the dialogue generation system 100, questions/queries, etc.

In addition to receiving the one or more participant registrations, the dialogue generator 136 may receive the configuration, which may include configuring an environment in which the dialogue generation system 100 is implemented (step 202 continued). For example, the configuration may include establishing network connections to the smart device 120 and/or the one or more data collection devices 110 utilized during a dialogue session, such as a smart device (e.g., smart phone, tablet, personal computer, etc.) for recording audio/video/etc. as well as displaying suggested responses and/or topics. The dialogue generator 136 may be further configured to save and/or store the participant registrations as profiles and reference, as well as add to, the profiles in subsequent dialogue generation sessions.

To further illustrate the operations of the dialogue generator 136, reference is now made to an illustrative example where the dialogue generator 136 aids a therapist in providing therapy to a patient. Here, the dialogue generator 136 receives patient information such as name, age, gender, location, etc., as well as psychological conditions relating to the desired therapeutic treatment. In addition, the dialogue generator 136 receives a configuration initializing a personal computer of the therapist as a device for recording the session and a smart watch for displaying to the therapist recommended responses.

The dialogue generator 136 may receive pre-dialogue scoring (step 204). In the example embodiment, the dialogue generator 136 utilizes pre-dialogue scoring as a baseline for determining an effectiveness, efficiency, and/or other scoring metrics of the generated (and overall) dialogue of the session. In embodiments, the pre-dialogue scoring can include scoring for a variety of categories and subcategories, which may be weighted based on an intention/goal of the session, as well as other considerations. In embodiments, the dialogue generator 136 may receive the pre-dialogue scoring via the dialogue generation client 122 and store the pre-dialogue scores in the scoring 132 via the network 108.

In furthering the earlier-introduced example, the dialogue generator 136 receives pre-dialogue scoring based on the Beck Depression Index (BDI).

The dialogue generator 136 may record session dialogue (step 206). In the example embodiment, the dialogue generator 136 records session dialogue using the one or more data collection devices 110 and may transfer the recorded session to the dialogue generation server 130 via the smart device 120 and the network 108. In embodiments, the dialogue generator 136 may process the audio, for example by transcribing audio to text, translating, removing noise, etc. In embodiments, the dialogue generator 136 may record audio, video, etc. and may retrieve the recorded session from the smart device 120 and/or the one or more data collection devices 110 at the end of the session, live in real time, at absolute or relative intervals, etc.

Continuing the earlier introduced example, the dialogue generator 136 records the dialogue session remotely via the personal computer of the therapist and extracts the recorded session live in real time.

The dialogue generator 136 may receive post-dialogue scoring (step 208). In the example embodiment, the dialogue generator 136 receives a scoring following the dialogue session as an indicator of an effectiveness, efficiency, etc. of the dialogue session. The dialogue generator 136 may then compare this post-dialogue scoring to the pre-dialogue scoring, while considering the session dialogue in between, in order to determine an effectiveness of the dialogue described in greater detail forthcoming.

Furthering the example above, the dialogue generator 136 receives post-dialogue scoring based on the Beck Depression Index.

The dialogue generator 136 may categorize session topics (step 210). In the example embodiment, the dialogue generator 136 may generate the predictive models 134 for various topics and subtopics of dialogue, including casual conversation, therapy, targeted conversation (e.g., sports, work, etc.), and the like. Accordingly, the dialogue generator 136 may categorize the recorded session such that the recorded session may be used to train a particular model. In embodiments, the dialogue generator 136 may receive a categorization from a participant, for example at configuration or during the dialogue session. In other embodiments, the dialogue generator 136 may categorize the session using methods, such as semantic similarity metrics trained with previously labelled sessions, topic modelling, keyword searching, pattern matching, etc., and a single session may be broken down into one or more categories as well as one or more subcategories, when applicable. In embodiments, the dialogue generator 136 may further consider information such as participant registration information when categorizing the session, for example considering the original query or reason a participant is using the dialogue generation system 100.

With reference to the example introduced above, the dialogue generator 136 applies semantic similarity metrics to the recorded session dialogue to categorize the session as a therapy session directed towards depression. Alternatively, the patient may indicate that they are seeking depression therapy, or the therapist may input that the dialogue session relates to therapy.

The dialogue generator 136 converts session dialogue into hashcode (step 208). In the example embodiment, the dialogue generator 136 converts the unconstrained text of the recorded dialogue (transcribing from audio, as needed) into a binary hashcode because, as explained above, while it is extremely difficult to infer an exact therapeutic response in the form of text, inferring a generalized representation for a therapeutic response is relatively easier, as the target to predict becomes lower dimensional. In the example embodiments, the dialogue generator 136 may convert the dialogue into hashcode using any suitable binary hashing functions, for example SHA256, SHA512, perlhash, etc. The resulting hashcode is a representation of the dialogue, which the dialogue generator 136 may then apply the predictive models 134 to. Moreover, the hashcode may be generated such that it is interpretable as well as useful for efficient search of text corresponding to the representation.

Continuing the example introduced above, the dialogue generator 136 converts the recorded and categorized session into a hashcode using an SHA256 hashing function.

The dialogue generator 136 may generate one or more predictive models (step 214). In generating and training the predictive models 134, the dialogue generator 136 may consider features that include the pre-dialogue scoring, the post-dialogue scoring, the session dialogue, and the session dialogue category in order to generate a model that most effectively, efficiently, etc., generates dialogue responses. For example, the dialogue generator 136 may determine that a post-dialogue scoring is improved relative to the pre-dialogue scoring in order to generate and weight a model that considers features found within the recorded dialogue, such features including responses, topics, moods, moods swings, topic discourse incoherence, logical derailment, etc. Conversely, the dialogue generator 136 may reduce a weight of features found to result in a worsened post-dialogue score relative to the pre-dialogue score. In addition, the dialogue generator 136 may be configured to utilize the weighted features of the predictive models 134 in order to generate suggested responses, topics, moods, etc. In some embodiments, the suggested responses may be extracted from recorded dialogue sessions having positive results, and therefore responses may simply be recycled. In more complex embodiments, the dialogue generator 136 may generate sentences from scratch, using the weighted features as cues indicating which types of semantics, syntax, and sentence structures to implement. In embodiments, the predictive models 134 may further consider vocal characteristics, including volume, pace, tone, inflection, etc., and provide suggestions for vocal characteristics in addition to the response itself.

Furthering the example above, the dialogue generator 136 generates a model for improving the effectiveness of a therapy session relating to depression based on the pre-scoring, the post-scoring, the recorded dialogue, and the dialogue category.

Figure 3:
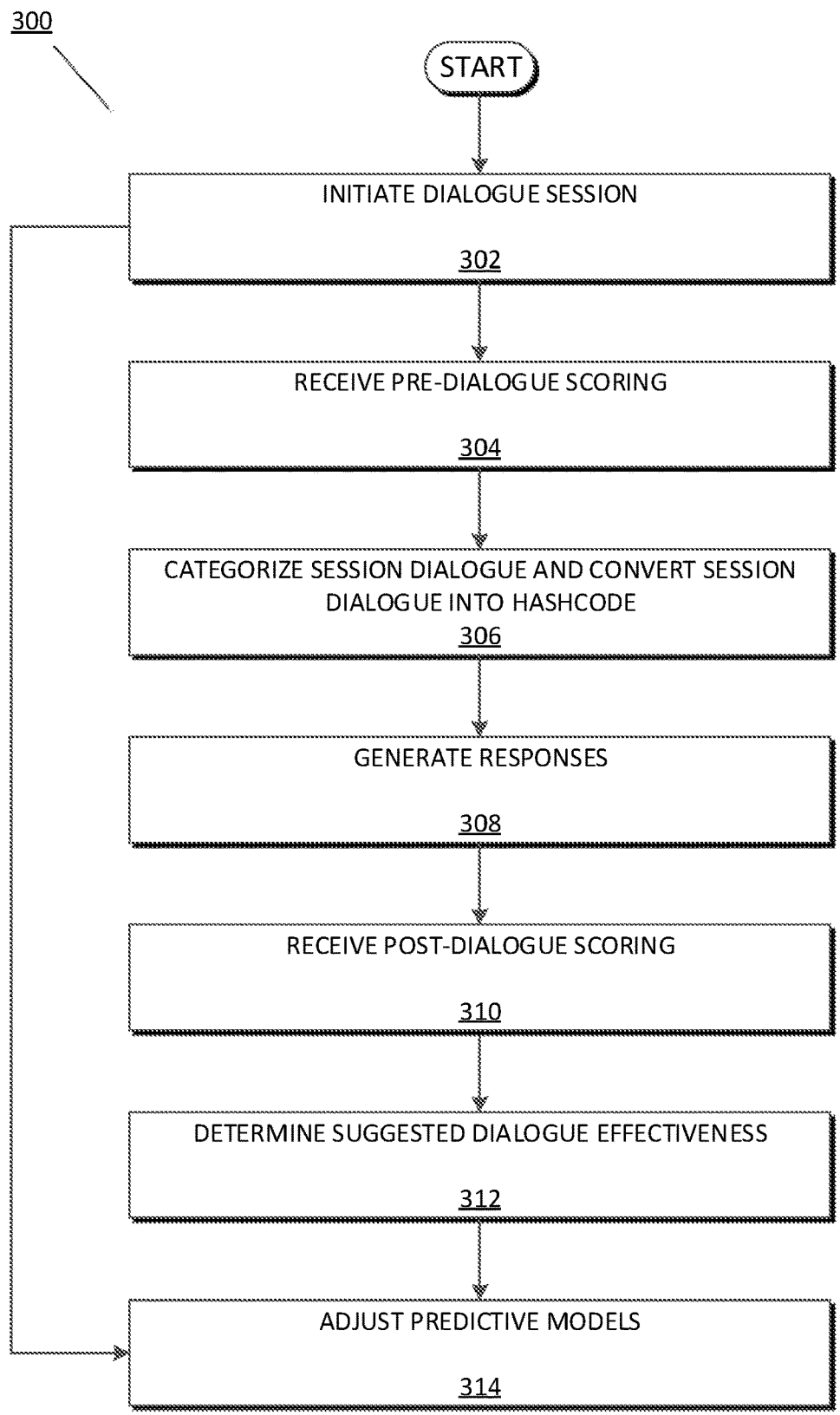
FIG. 3 depicts a flowchart 300 illustrating the operations of the dialogue generator 126 of the dialogue generation system 100 in generating dialogue via hashing functions, in accordance with exemplary embodiments.

FIG. 3 depicts a flowchart 300 illustrating the operations of a dialogue generator 126 of the dialogue generation system 100 in generating dialogue via hashing functions, in accordance with exemplary embodiments.

The dialogue generator 136 may initiate a dialogue session (step 302). Similar to the manner in which the dialogue generator 136 initiates a dialogue session during training at step 202 of the flowchart 200, initiating the dialogue session may involve the dialogue generator 136 receiving one or more participant registrations and/or a configuration of the dialogue generation system 100, both via the dialogue generation client 122 and the network 108. In particular, the participant registrations may include demographic information of dialogue participants, such as participant name, gender, date of birth, location, etc., as well as other information such as health and diagnosis information, previous interactions with participants and/or the dialogue generation system 100, reasons for utilizing the dialogue generation system 100, questions/queries, etc.

In addition to receiving the one or more participant registrations, the dialogue generator 136 may receive the configuration, which may include configuring an environment in which the dialogue generation system 100 is implemented (step 202 continued). For example, the configuration may include establishing network connections to the smart device 120 and/or the one or more data collection devices 110 utilized during a dialogue session, such as a smart device (e.g., smart phone, tablet, personal computer, etc.) for recording audio/video/etc. as well as displaying suggested responses and/or topics. The dialogue generator 136 may be further configured to save and/or store the participant registrations as profiles and reference, as well as add to, the profiles in subsequent dialogue generation sessions.

To further illustrate the operations of the dialogue generator 136, reference is now made to an illustrative example where the dialogue generator 136 aids a therapist in providing therapy to a patient. Here, the dialogue generator 136 receives patient information such as name, age, gender, location, etc., as well as psychological conditions relating to the desired therapeutic treatment. In addition, the dialogue generator 136 receives a configuration initializing a personal computer of the therapist as a device for recording the session and a smart watch for displaying to the therapist recommended responses.

The dialogue generator 136 may receive pre-dialogue scoring (step 304). Similar to the manner in which the dialogue generator 136 receives a pre-dialogue scoring during training at step 204 of the flowchart 200, the dialogue generator 136 may receive and utilize the pre-dialogue scoring as a baseline for determining an effectiveness, efficiency, and/or other metrics of the generated (and overall) dialogue of the session. In embodiments, the pre-dialogue scoring can include scoring for a variety of categories and subcategories, which may be weighted based on an intention/goal of the session, as well as other considerations. In embodiments, the dialogue generator 136 may receive the pre-dialogue scoring via the dialogue generation client 122 and store the pre-dialogue scores in the scoring 132 via the network 108.

In furthering the earlier-introduced example, the dialogue generator 136 receives pre-dialogue scoring based on the Beck Depression Index (BDI).

The dialogue generator 136 may categorize the dialogue session and convert the dialogue session to hashcode (step 306). Similar to the manner in which the dialogue generator 136 categorizes the dialogue during training at step 210 of the flowchart 200, the dialogue generator 136 categorizes the dialogue session in real time in order to determine a topic of the dialogue session and identify an applicable model. As previously mentioned, the dialogue generator 136 may generate the one or more predictive models 134 relating to various forms of dialogue, whether it be casual conversation, negotiation, targeted discussion, therapy, etc. Accordingly, the dialogue generator 136 determines a topic of the dialogue in order to select an appropriate model of the predictive models 134 to apply to the dialogue. In addition, the dialogue generator 136 may further convert the session dialogue into hashcode such that the predictive models 134 may be applied. Similar to the manner in which the dialogue generator 136 converts the dialogue to hashcode during training at step 212 of the flowchart 200, the dialogue generator 136 may implement any known hashing function in order to convert the dialogue.

Returning to the previously-introduced example, the dialogue generator 136 categorizes the dialogue session as relating to depression, and converts the dialogue to hashcode using an SHA256 hashing algorithm.

The dialogue generator 136 may generate one or more responses (step 308). In embodiments, the dialogue generator 136 may generate one or more responses by applying a model of the predictive models 134 of the same topic to the converted hashcode of the dialogue session. Based on the topic of the dialogue and features found within, the dialogue generator 136 may apply an applicable model of the predictive models 134 in order to output a suggested response intended to improve a post-dialogue scoring. In embodiments, the suggested response may be displayed to a participant using the smart device 120 or the one or more data collection devices 110 via the dialogue generation client 122 and the network 108. Moreover, the dialogue generator 136 may be configured to provide multiple suggested responses, allowing a participant to choose from a selection for a best response. In embodiments, such suggested responses may be ranked based on a most likely response to further a goal of the dialogue.

Furthering the earlier-introduced example, the dialogue generator 136 applies a predictive model relating to depression to the dialogue hashcode to output one or more suggested responses, including a suggestion to take a different point of view to gain insights, to consider whether a particular negative emotion may be justified, to clarify an explanation, to request to follow up/continue, or to exclaim "aha" in order to express assent or an invitation to keep talking.

The dialogue generator 136 may receive post-dialogue scoring (step 310). Similar to the manner in which the dialogue generator 136 may receive post-dialogue scoring during training at step 208 of the flowchart 200, the dialogue generator 136 receives a scoring following the dialogue session as an indicator of an effectiveness, efficiency, etc. of the dialogue session. The dialogue generator 136 may then compare this post-dialogue scoring to the pre-dialogue scoring, while considering the session dialogue in between, in order to determine an effectiveness of the dialogue.

In furthering the earlier-introduced example, the dialogue generator 136 receives post-dialogue scoring based on the Beck Depression Index (BDI).

The dialogue generator 136 determines a suggested dialogue effectiveness (step 312). In the example embodiment, the dialogue generator 136 may determine a suggested dialogue effectiveness by comparing the baseline pre-dialogue scoring to the post-dialogue scoring to determine whether the scores have improved or worsened.

With reference to the example above, the dialogue generator 136 compares the pre-dialogue BDI scoring with the post-dialogue BDI scoring.

The dialogue generator 136 may adjust predictive models (step 314). In the example embodiment, the dialogue generator 136 may adjust the predictive models 134 based on the determined dialogue effectiveness. For example, if the suggested dialogue resulted in a greatly improved post-dialogue scoring, then the dialogue generator 136 may increase a weight associated with features relied on in generating the suggested response. Alternatively, the dialogue generator 136 may decrease a weight associated with relied on features if the post-dialogue scoring has worsened relative to the pre-dialogue scoring.

Referring now to the previously introduced illustrative example, the dialogue generator 136 increases a weight of features relied upon if the post-dialogue scoring is improved relative to the pre-dialogue scoring, while decreasing a weight of features relied upon if the post-dialogue scoring has worsened relative to the pre-dialogue scoring.

Figure 4:
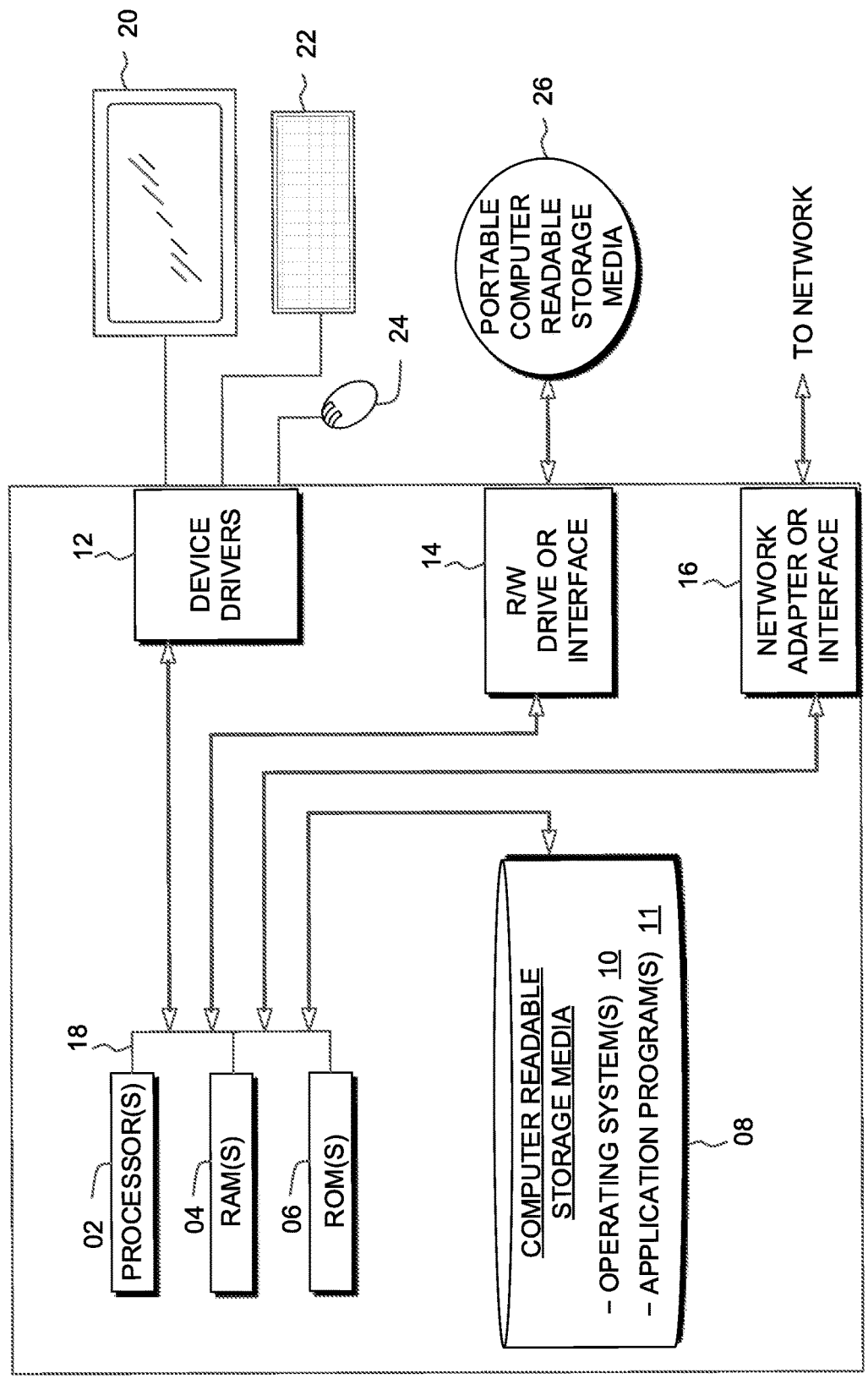
FIG. 4 depicts a block diagram depicting the hardware components of the dialogue generation system 100 of FIG. 1, in accordance with example exemplary embodiments.

FIG. 4 depicts a block diagram of devices within the dialogue generation system 100 of FIG. 1, in accordance with an embodiment of the present invention. It should be appreciated that FIG. 4 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
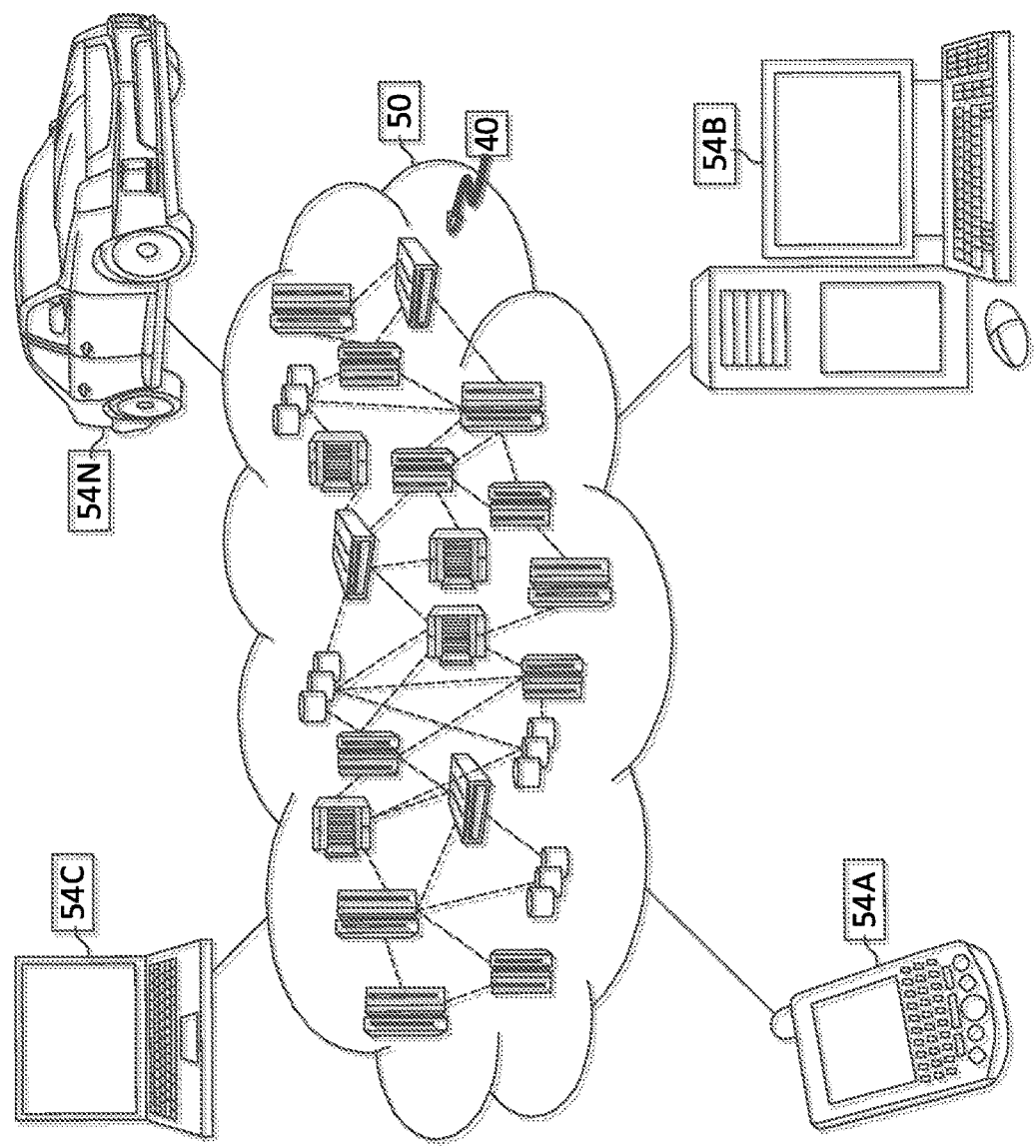
FIG. 5 depicts a cloud computing environment that, in accordance with an exemplary embodiments.

Referring now to FIG. 5, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 40 and cloud computing environment 50 can communicate with any type of computerized device over any type of network and/or network addressable connection (e.g., using a web browser).

Figure 6:
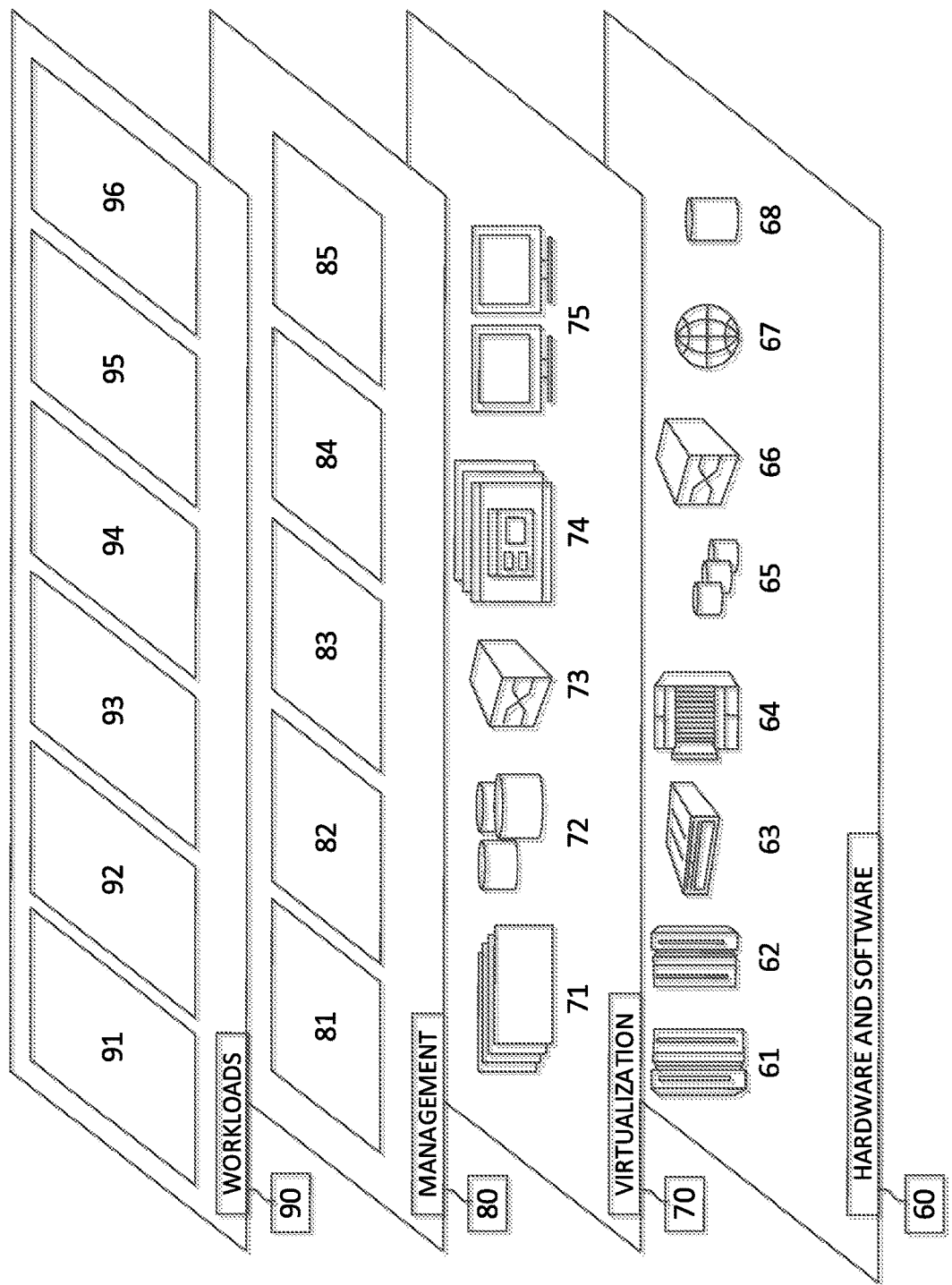
FIG. 6 depicts abstraction model layers, in accordance with exemplary embodiments.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and hashcode processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for generating dialogue via hashing functions, the method comprising:
   detecting dialogue between one or more participants;
   determining at least one topic of the dialogue;
   determining one or more models that are weighted based on the at least one topic of the dialogue and dialogue scores from historic participants related to the effectiveness of the determined one or more models in a prior dialogue, wherein the dialogue scores each include a pre-dialogue score and a post-dialogue score;
   converting the dialogue to a hashcode; and
   determining one or more responses to the dialogue and suggested vocal characteristics thereof by applying the determined one or more models to the hashcode, wherein the determined one or more models correlate one or more hashcodes with the one or more responses, wherein the one or more responses are determined based on features of the prior dialogue associated with effective dialogue scores in which the post-dialogue score is improved in comparison to the pre-dialogue score.

2. The method of claim 1, further comprising:
   categorizing the dialogue, and wherein applying the determined one or more models to the hashcode is based on the categorization of the dialogue.

3. The method of claim 2, wherein categorizing the dialogue is performed via semantic similarity metrics.

4. The method of claim 1, further comprising:
   displaying the one or more responses.

5. The method of claim 1, further comprising:
   modifying the determined one or more models based on the dialogue effectiveness.

6. The method of claim 1, wherein converting the dialogue to hashcode is performed via one or more hashing functions.

7. A computer program product for generating dialogue via hashing functions, the
   computer program product comprising:
   one or more non-transitory computer-readable storage media and program instructions stored on the one or more non-transitory computer-readable storage media which perform a method, the method comprising:
   detecting dialogue between one or more participants;
   determining at least one topic of the dialogue;
   determining one or more models that are weighted based on the at least one topic of the dialogue and dialogue scores from historic participants related to the effectiveness of the determined one or more models in a prior dialogue, wherein the dialogue scores each include a pre-dialogue score and a post-dialogue score;

converting the dialogue to a hashcode; and determining one or more responses to the dialogue and suggested vocal characteristics thereof by applying the determined one or more models to the hashcode, wherein the determined one or more models correlate one or more hashcodes with the one or more responses, wherein the one or more responses are determined based on features of the prior dialogue associated with effective dialogue scores in which the post-dialogue score is improved in comparison to the pre-dialogue score.

8. The computer program product of claim 7, further comprising:

categorizing the dialogue, and wherein applying the determined one or more models to the hashcode is based on the categorization of the dialogue.

9. The computer program product of claim 8, wherein categorizing the dialogue is performed via semantic similarity metrics.

10. The computer program product of claim 7, further comprising:

displaying the one or more responses.

11. The computer program product of claim 7, further comprising:

modifying the determined one or more models based on the dialogue effectiveness.

12. The computer program product of claim 7, wherein converting the dialogue to hashcode is performed via one or more hashing functions.

13. A computer system for generating dialogue via hashing functions, the computer system comprising:

one or more computer processors, one or more computer-readable storage media, and program instructions stored on one or more of the computer-readable storage media for execution by at least one of the one or more processors which perform a method, the method comprising:

detecting dialogue between one or more participants;

determining at least one topic of the dialogue;

determining one or more models that are weighted based on the at least one topic of the dialogue and dialogue scores from historic participants related to the effectiveness of the determined one or more models in a prior dialogue, wherein the dialogue scores each include a pre-dialogue score and a post-dialogue score;

converting the dialogue to a hashcode; and determining one or more responses to the dialogue and suggested vocal characteristics thereof by applying the determined one or more models to the hashcode, wherein the determined one or more models correlate one or more hashcodes with the one or more responses, wherein the one or more responses are determined based on features of the prior dialogue associated with effective dialogue scores in which the post-dialogue score is improved in comparison to the pre-dialogue score.

14. The computer system of claim 13, further comprising:

categorizing the dialogue, and wherein applying the determined one or more models to the hashcode is based on the categorization of the dialogue.

15. The computer system of claim 14, wherein categorizing the dialogue is performed via semantic similarity metrics.

16. The computer system of claim 13, further comprising:

displaying the one or more responses.

17. The computer system of claim 13, further comprising:

modifying the determined one or more models based on the dialogue effectiveness.

\* \* \* \* \*